US010207011B2

(12) United States Patent
Ganetzky et al.

(10) Patent No.: US 10,207,011 B2
(45) Date of Patent: Feb. 19, 2019

(54) METHODS, SYSTEMS, AND DEVICES FOR AN INVERTEBRATE MODEL OF TRAUMATIC BRAIN INJURY

(71) Applicant: WISCONSIN ALUMNI RESEARCH FOUNDATION, Madison, WI (US)

(72) Inventors: Barry S. Ganetzky, Madison, WI (US); David A. Wassarman, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 474 days.

(21) Appl. No.: 14/314,505

(22) Filed: Jun. 25, 2014

(65) Prior Publication Data

US 2014/0377183 A1 Dec. 25, 2014

Related U.S. Application Data

(60) Provisional application No. 61/839,215, filed on Jun. 25, 2013.

(51) Int. Cl.
*A61K 49/00* (2006.01)
*G01N 33/50* (2006.01)
*A61B 5/00* (2006.01)
*A61D 3/00* (2006.01)

(52) U.S. Cl.
CPC ........ *A61K 49/0008* (2013.01); *A61B 5/4064* (2013.01); *A61B 5/4848* (2013.01); *A61D 3/00* (2013.01); *G01N 33/5091* (2013.01); *A61B 2503/40* (2013.01); *A61B 2503/42* (2013.01); *G01N 2333/43573* (2013.01); *G01N 2500/00* (2013.01); *G01N 2800/2814* (2013.01)

(58) Field of Classification Search
CPC ................ A61K 49/0004; A61K 49/00; A61K 49/0008; A01K 2217/05; G01N 33/5088; G01N 33/5091; G01N 2333/43573; G01N 2500/00; G01N 2800/2814; A61D 3/00; A61B 5/4064; A61B 5/4848; A61B 2503/40; A61B 2503/42
USPC ............. 424/1.11, 1.49, 1.65, 1.69, 9.1, 9.2; 514/1, 1.1; 530/300
See application file for complete search history.

(56) References Cited

U.S. PATENT DOCUMENTS

| | | | | |
|---|---|---|---|---|
| 6,951,924 B2 * | 10/2005 | Rosen | ..................... | C07K 14/47 435/326 |
| 2004/0143855 A1 * | 7/2004 | Tononi | ................. | A01K 67/033 800/8 |
| 2010/0263599 A1 | 11/2010 | Yanik et al. | | |
| 2014/0107523 A1 * | 4/2014 | Petraglia | .................. | A61D 3/00 600/553 |

OTHER PUBLICATIONS

Katzenberger et al, PNAS, Oct. 14, 2013, pp. E4152-E4159.*
Cernak, The American Society for Experimental NeuroTherapeutics, Inc, 2005, vol. 2, pp. 410-422.*
Hirth, CNS & Neurological Disorders—Drug Targets, vol. 9, pp. 504-523. (Year: 2010).*
Hockey et al, Rocky Mountain Bioengineering Symposium & International ISA Biomedicl Sciences Instrumentation Symposium. Colorado Springs, Colorado, Apr. 5-7, 2013, pp. 134-140. (Year: 2013).*
Fang et al, Annu. Rev. Cell Dev. Biol., vol. 28, pp. 575-597. (Year: 2012).*
Stork et al, Cold Spring Harbor Protocols, pp. 1-17. (Year: 2012).*
Reichert, Brain Research, vol. 66, pp. 491-494. (Year: 2005).*
Lessing et al, Nat. Rev. Genet., vol. 10, No. 6, pp. 1-26. (Year: 2009).*
Blennow, Kaj, et al. "The neuropathology and neurobiology of traumatic brain injury." Neuron 76.5 (2012): 886-899.
Bushey, Daniel, et al. "From genetics to structure to function: exploring sleep in *Drosophila*." International review of neurobiology 99 (2011): 213-244.
Castriotta, Richard J. et al. "Sleep disorders in patients with traumatic brain injury." CNS drugs 25.3 (2011): 175-185.
Cernak, Ibolja. "Animal models of head trauma." NeuroRx 2.3 (2005): 410-422.
Dahmann (2008), *Drosophila*: Methods and Protocols (Methods in Molecular Biology), Humana Press pp. 1-4.
Dankert, Heiko, et al. "Automated monitoring and analysis of social behavior in *Drosophila*." Nature methods 6.4 (2009): 297-303.
Dietzl, Georg, et al. "A genome-wide transgenic RNAi library for conditional gene inactivation in *Drosophila*." Nature 448.7150 (2007): 151-156.
Gilestro, Giorgio F. "Video tracking and analysis of sleep in *Drosophila melanogaster*." Nature protocols 7.5 (2012): 995-1007.
Hammond, Flora M., et al. "Change and predictors of change in communication, cognition, and social function between 1 and 5 years after traumatic brain injury." The Journal of head trauma rehabilitation 19.4 (2004): 314-328.
Harrison-Felix, Cynthia, et al. "Mortality following rehabilitation in the traumatic brain injury model systems of care." NeuroRehabilitation 19.1 (2004): 45-54.
Helmy, Adel, et al. "Cytokines and innate inflammation in the pathogenesis of human traumatic brain injury." Progress in neurobiology 95.3 (2011): 352-372.
Hockey, K. S., et al. "A new model for mild blast injury utilizing *Drosophila melanogaster*-biomed 2013." Biomedical sciences instrumentation 49 (2012): 134-140.
Jang, Sung Ho. "Review of motor recovery in patients with traumatic brain injury." NeuroRehabilitation 24.4 (2009): 349-353.
Katzenberger, Rebeccah J., et al. "A *Drosophila* model of closed head traumatic brain injury." Proceedings of the National Academy of Sciences 110.44 (2013): E4152-E4159.

(Continued)

*Primary Examiner* — D. L. Jones
(74) *Attorney, Agent, or Firm* — Quarles & Brady, LLP

(57) ABSTRACT

Described herein are methods, systems, and devices for identifying agents and genetic pathways that modulate the effects of traumatic brain injury (TBI) in invertebrate model systems having a brain, e.g., *Drosophila* or *C. elegans*.

17 Claims, 10 Drawing Sheets

(56) References Cited

OTHER PUBLICATIONS

MacKay, Trudy FC, et al. "The *Drosophila melanogaster* genetic reference panel." Nature 482.7384 (2012): 173-178.
McGuire, Sean E., et al. "Gene expression systems in *Drosophila*: a synthesis of time and space." Trends in Genetics 20.8 (2004): 384-391.
Millis, Scott R., et al. "tong-term neuropsychological outcome after traumatic brain injury." The Journal of head trauma rehabilitation 16.4 (2001): 343-355.
Murakami, Satoshi, et al. "Optimizing *Drosophila* olfactory learning with a semi-automated training device." Journal of neuroscience methods 188.2 (2010): 195-204.
Nichols, Charles D., et al. "Methods to assay *Drosophila* behavior." Journal of visualized experiments: JoVE 61 (2012).
Petersen, Andrew J., et al. "*Drosophila* innate immune response pathways moonlight in neurodegeneration." Fly 6.3 (2012): 169-172.
Rival, Thomas, et al. "Decreasing Glutamate Buffering Capacity Triggers Oxidative Stress and Neuropil Degeneration in the *Drosophila* Brain." Current biology 14.7 (2004): 599-605.
Sawa H., Korswagen H., C. "Wnt signaling in C. elegans", (Dec. 9, 2013), WormBook, ed. The C. elegans Research Community, Worm Book, doi/10.1895/wormbook.1.7.2, http://www.wormbook.org.
Shively, Sharon, et al. "Dementia resulting from traumatic brain injury: what is the pathology?." Archives of neurology 69.10 (2012): 1245-1251.
Simon, Anne F., et al. "A simple assay to study social behavior in *Drosophila*: measurement of social space within a group1." Genes, Brain and Behavior 11.2 (2012): 243-252.
Todd, Peter K., et al. "RNA—mediated neurodegeneration in repeat expansion disorders." Annals of neurology 67.3 (2010): 291-300.
Tzou, Phoebe, et al. "Tissue-Specific Inducible Expression of Antimicrobial Peptide Genes in *Drosophila* Surface Epithelia." Immunity 13.5 (2000): 737-748.
Xiong, Ye, Asim Mahmood, and Michael Chopp. "Animal models of traumatic brain injury." Nature Reviews Neuroscience 14.2 (2013): 128-142.
Zordan, M. A., et al. "Monitoring and analyzing *Drosophila* circadian locomotor activity." Methods in molecular biology (Clifton, NJ) 362 (2006): 67-81.
Gladstone, Mara, and Tin Tin Su. "Chemical genetics and drug screening in Drosophila cancer models." Journal of Genetics and Genomics 38.10 (2011): 497-504.
Kasai, Yumi, and Ross Cagan. "*Drosophila* as a tool for personalized medicine: a primer." Personalized medicine 7.6 (2010): 621-632.
Lessing, Derek, and Nancy M. Bonini. "Maintaining the brain: insight into human neurodegeneration from *Drosophila melanogaster* mutants." Nature Reviews Genetics 10.6 (2009): 359-370.
Kahsai, Lily, and Troy Zars. "Learning and memory in *Drosophila*: behavior, genetics, and neural systems." Int Rev Neurobiol 99 (2011): 139-167.
O'Kane, Cahir J. "*Drosophila* as a model organism for the study of neuropsychiatric disorders." Molecular and functional models in neuropsychiatry. Springer Berlin Heidelberg, 2011. 37-60.
Fang, Yanshan, and Nancy M. Bonini. "Axon degeneration and regeneration: insights from *Drosophila* models of nerve injury." Annual review of cell and developmental biology 28 (2012): 575-597.
Hirth, Frank. "*Drosophila melanogaster* in the study of human neurodegeneration." CNS & neurological disorders drug targets 9.4 (2010): 504.

Fernandez-Hernandez, I., et al. New neurons for injured brains? The emergence of new genetic model organisms to study brain regeneration, Neuroscience and Biobehavioral Reviews, 2015, 56:62-72.
Chan, S., et al. A case study of magnetic resonance imaging of cerebrovscular reactivity: A powerful imaging marker for mild traumatic brain injury, Brain Injury, 2014, 29(3):403-407.
Carey, J.R., et al. Diet shapes mortality response to trauma in old tephritid fruit flies, PLoS One, 2016, 11(7): e0158468.
Srinivasan, N., et al. Actin is an evolutionarily-conserved damage-associated molecular pattern that signals tissue injury in *Drosophila melanogaster*, eLIFE, 2016, 5:e19662.
Gasch, A.P., et al. The power of natural variation for model organism biology, Cell Press Trends in Genetics, 2016, 32(3), 147-154.
Kashio, et al., How tissue damage MET metabolism: Regulation of the systemic damage response, Fly, 2016, 11 (1):27-36.
Li, D., et al., miR-285-Yki/Mask double-negative feedback loop mediates blood-brain barrier integrity in *Drosophila*, PNAS, 2017, E2365-E2374.
Liu, et al., Organ-to-organ communication: A *Drosophila* gastrointestinal tract perspective, Frontiers in Cell and Developmental Biology, 2017, 5(29).
MacMillan, H. A., et al., Thermal acclimation mitigates cold-induced paracellular leak from the *Drosophila* gut, Scientific Reports, 201, 7:8807.
Przekwas, A., et al., Synaptic mechanisms of blast-induced brain injury, Frontiers in Neurology, 2016, 7(2).
Adams, et al., Temporal profile of intracranial pressure and cerebrovascular reactivity in severe traumatic brain injury and association with fatal outcome: An observational study, PLoS Medicine, 2017, 14(7):e1002353.
Barekat, A., et al., Using *Drosophila* as an integrated model to study mild repetative traumatic brain injury, Scientific Reports, 2016, 6:25252.
Bonini, N. et al., Device to produce traumatic brain injury in model organisms, Penn Center for Innovation, 2017.
Sun, et al., A novel method to model chronic traumatic encephalopathy in *Drosophila*, Journal of Visualized Experiments, 2017, 125, e55602.
Kanchan, et al., Role of acamprosate in traumatic brain injury: A study in *Drosophila melanogaster* using high impact trauma model, International Journal of Pharmaceutic Science Research, 2016, 1(6):47-52.
Sen, et al., Traumatic brain injury causes retention of long introns in metabolic genes vis regulation of intronic histone 3 lysine 36 methylation levels in the sub-acute phase of injury, bioRxin, 2016.
Katzenberger, R. J., et al., A *Drosophila* model of closed head traumatic brain injury, PNAS, 2013, 110(44), E4152-E4159.
Katzenberger, R.J., et al., A method to inflict closed head traumatic brain injury in *Drosophila*, Journal of Visualized Experiments, 2015, (100, e52905.
Katzenberger, R. J., et al., Death following traumatic brain injury in *Drosophila* is associated with intestinal barrier dysfunction, eLIFE, 2015, e04790.
Katzenberger, R. J., et al. Age and diet affect genetically separable secondary injuries that cause acute mortality following traumatic brain injury in *Drosophila*, Genes Genomes Genetics, 2016, 6, 4151-4166.
Katzenberger, R. J., et al., The gut reaction to traumatic brain injury, Fly, 2015, 9(2):68-74.
Ganetsky, B., et al., Non-mammalian animal models offer new perspectives on the treatment of TBI, Curr Phys Med Rehabil Rep, 2016, 4(1):1-4.

\* cited by examiner

METHODS, SYSTEMS, AND DEVICES FOR AN INVERTEBRATE MODEL OF TRAUMATIC BRAIN INJURY

CROSS-REFERENCE TO RELATED APPLICATIONS

This application claims priority to U.S. Provisional Patent Application Ser. No. 61/839,215 filed Jun. 25, 2013, which is incorporated by reference herein in its entirety.

STATEMENT REGARDING FEDERALLY SPONSORED RESEARCH OR DEVELOPMENT

This invention was made with government support under NS059001, NS015390 and AG033620 awarded by the National Institutes of Health. The government has certain rights in the invention.

BACKGROUND

Traumatic brain injury (TBI) is a serious public health problem resulting in death or permanent disability. In fact, according to the Centers for Disease Control and Prevention, in the U.S. alone, about two million TBIs occur every year either as an isolated injury or along with other injuries. Further, TBI is a contributing factor to about one third of all injury-related deaths in the U.S. TBI can cause neurological disorders such as neurodegeneration, memory deficits, and sleep disorders, as well as non-neurological disorders such as systemic metabolic dysregulation.

Yet, despite the urgent need for effective therapeutics for the treatment of TBI, none have been developed to date. Drug candidates tested in established animal models (predominantly rats and mice) have all failed in clinical trials. The failure to develop therapies is likely due to the complexity of TBI, both in terms of the severity and spatial distribution of injury to the brain and the elaborate responses of the brain to injury. In addition, a major disadvantage of established TBI models is that they are not amenable to large phenotypic screens, e.g., small molecule library screens, RNAi screens, or mutagenesis screens. Thus, there is an ongoing need for model systems of TBI that allow for medium to high-throughput identification of TBI-relevant genetic pathways and candidate therapeutic agents.

BRIEF SUMMARY OF THE INVENTION

The invention relates generally to methods for identifying agents and genetic pathways that modulate impact-associated phenotypes in an invertebrate model of traumatic brain injury (TBI). The invention also relates to systems and devices for modeling TBI in suitable invertebrate organisms.

Accordingly, in a first aspect described herein is an in vivo screening method for identifying a candidate therapeutic agent for treatment or prevention of traumatic brain injury, where the method includes the steps of: (i) subjecting one or more individuals of an invertebrate species having a brain to a controlled impact; (ii) dosing the one or more individuals with a test agent before or after the controlled impact; (iii) assessing an impact-associated phenotype in the one or more dosed individuals following the dosing and the controlled impact; and (iv) indicating that the test agent is a candidate therapeutic agent for treatment or prevention of traumatic brain injury if the impact-associated phenotype assessed in the one or more dosed individuals is reduced relative to the impact-associated phenotype assessed in individuals that have not been dosed with a test agent.

In some embodiments of the first aspect, controlled impact occurs at a velocity of about 0.5 m/s to about 20 m/s. In some embodiments, step (i) includes subjecting the one or more individuals to multiple controlled impacts.

In some embodiments, in step (ii) the dosing is performed before the controlled impact. In other embodiments, dosing is performed after the controlled impact.

In some embodiments, the one or more individuals are *Drosophila* flies. In some embodiments, the *Drosophila* flies are at least 20 days old. In some embodiments, the age range of the *Drosophila* flies to be used ranges from at least about one day to about 30 days, e.g., about 5 days, 7 days, 8 days, 10 days, 12 days, 15 days, 18 days, 20 days, 24 days, 26 days, or another age from at least about one day to about 30 days old. In other embodiments, the one or more individuals are *C. elegans* worms.

In some embodiments, step (i) comprises subjecting individuals from at least two different genetic backgrounds to the controlled impact.

In some embodiments, the impact-associated phenotype includes one or more of lethality, an immune response, neurodegeneration, a sleep abnormality, a circadian abnormality, a learning deficit, a memory deficit, a social behavior deficit, a motor behavior deficit, changes in intestinal barrier permeability, changes in gene expression, microtubule structural changes, changes in enzymatic activity, changes in phosphorylation or other post-translational modifications, and changes in the concentration of small metabolites.

In some embodiments the controlled impact is generated by an angular motion. In other embodiments the controlled impact is generated by a linear motion. In some embodiments, the controlled impact is a computer-controlled impact.

In some embodiments, the one or more individuals in step (i) are enclosed within a container, and the container is subjected to the controlled impact. In some embodiments, where the container includes a short axis and a long axis, the container is subjected to the controlled impact along its long axis. In other embodiments, the container is subjected to the controlled impact along its short axis.

In some embodiments, the one or more individuals subjected to the controlled impact comprises at least two groups of individuals. In some embodiments, at least two groups of individuals are simultaneously subjected to the controlled impact.

In a second aspect described herein is a method for identifying a transgene that modulates an impact-associated phenotype, comprising:

(i) subjecting one or more individuals of an invertebrate species having a brain to a controlled impact, wherein the individuals comprise a transgene; (ii) expressing the transgene in the one or more individuals before or after the controlled impact; (iii) assessing an impact-associated phenotype in the one or more individuals following expression of the transgene and the controlled impact; and (iv) indicating that the transgene modulates the impact-associated phenotype if the impact-associated phenotype assessed in the one or more individuals expressing the transgene differs from the impact-associated phenotype assessed in individuals that do not express the transgene.

In some embodiments of the second aspect the one or more individuals are *Drosophila* flies. In other embodiments, the one or more individuals are *C. elegans* worms In some embodiments, the transgene comprises an expression cassette for a polypeptide. In some embodiments, the polypeptide is a polypeptide associated with a neurodegenerative disease. In some embodiments, the polypeptide associated with a neurodegenerative disease is hAPP, hAbeta1-42, a hTau, a hSynuclein, hHuntingtin, a hTDP-43, a hSOD, hLRRK2, a hGSK3β, or a polyQ polypeptide comprising at least 35 contiguous glutamines. In other embodiments, the transgene comprises an expression cassette for an RNAi. In other embodiments, the transgene includes a gene for a non-coding RNA, e.g., non-coding RNAs or untranslated portions (5' or 3' UTR) portions of coding RNA that include at least 40 repeat motifs, e.g., CTG, CCTG, CAG, ATTCT.

In a third aspect described herein is a method for identifying an invertebrate mutant carrying a modifier mutation that modulates an impact-associated phenotype, comprising the steps of: (i) subjecting one or more mutants of an invertebrate species having a brain to a controlled impact, wherein the one or more mutants are from a mutant line carrying at least one mutation relative to a control line; (ii) assessing an impact-associated phenotype in the one or more mutants; and (iii) indicating that the mutant line carries a modifier mutation if the impact-associated phenotype assessed in the mutant is attenuated or enhanced relative to the impact-associated phenotype assessed in a control line.

In some embodiments of the third aspect, the one or more mutants are *Drosophila* flies. In other embodiments, the one or more mutants are *C. elegans* worms.

In some embodiments, the mutant line is a randomly mutagenized mutant line.

In some embodiments of the third aspect, the method also includes mapping the modifier mutation.

In a fourth aspect described herein is a controlled impact trauma (CIT) system comprising: (i) a base; (ii) a deceleration assembly comprising a strike surface; (iii) an adaptor assembly holding one or more containers containing a plurality of individuals of an invertebrate species having a brain; and (iv) an acceleration assembly coupled between the base and the adaptor assembly, and configured to accelerate the one or more containers held in the adaptor assembly toward the strike surface to generate a controlled impact of the one or more containers on the strike surface at a predetermined, adjustable impact velocity.

In some embodiments of the fourth aspect, the individuals are individuals dosed with a test agent. In some embodiments, the individuals are *Drosophila* flies In some embodiments, the acceleration assembly is configured to accelerate the one or more containers to a predetermined impact velocity of about 0.5 m/s to about 20 m/s.

In some embodiments, each container comprises a digital data tag. In some embodiments, the digital tag is an RFID tag.

In some embodiments, the strike surface comprises rubber or another material having a young's modulus no greater than about 2 GPa.

In some embodiments, the adaptor assembly in the CIT holds at least two containers, each container comprising the one or more individuals.

In some embodiment the acceleration assembly comprises a spring. In other embodiments, the acceleration assembly comprises an electric motor.

In a fifth aspect described herein is a controlled impact trauma (CIT) device, comprising: (i) a base; (ii) a deceleration assembly comprising a strike surface; (iii) an adaptor assembly configured to hold at least one container of dimensions suitable to contain a plurality of viable *Drosophila* flies; and (iv) an acceleration assembly coupled between the base and the adaptor assembly, and configured to accelerate, when in use, the one or more containers held in the adaptor assembly toward the strike surface to generate a controlled impact of the at least one container on the strike surface at a predetermined, adjustable velocity.

In some embodiments of the fifth aspect, the strike surface is made of rubber or a material having a young's modulus no greater than about 2 GPa.

In some embodiments, the acceleration assembly comprises a spring. In some embodiments, the deceleration assembly is coupled to the base.

In some embodiments, the adaptor assembly is configured to hold at least two containers.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
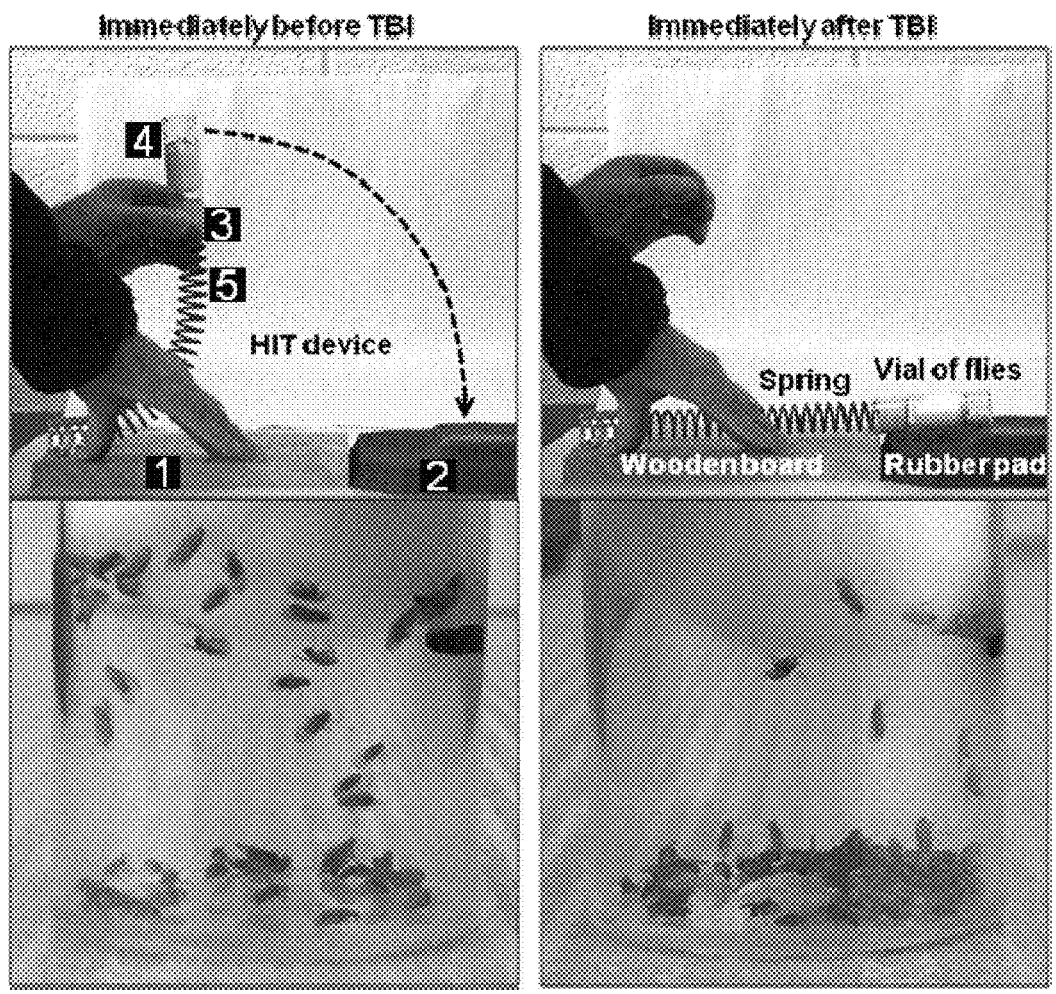
FIG. 1 shows the set-up and use of an exemplary, non-limiting embodiment of a controlled impact trauma ("CIT") device for use in the described methods. This device consists of a metal spring (acceleration assembly—labeled "5") that is clamped at one end to a wooden board (base—"1") and has a free end positioned over a hard rubber pad. (strike surface—"2"). A standard plastic vial (container—"4") containing unanesthetized flies is connected to the free end of the spring (adaptor assembly—"3"). The flies are confined to the bottom quarter of the vial by a stationary cotton ball. When the spring is deflected and released, the vial impacts the hard rubber pad, and a mechanical force is delivered to the flies as they contact the vial wall.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The present invention is based on the unexpected finding that many of the biological responses to impact-induced trauma, (e.g., traumatic brain injury) observed in mammals are conserved in certain invertebrate species, e.g., *Drosophila*. Such responses include, an increased and age-sensitive mortality rate, neurodegeneration, and activation of the innate immune system. Thus, as described herein, invertebrate species that have a brain, and are amenable to genetic analysis, e.g., *Drosophila* and *C. elegans*, can be used for chemical and genetic screens to identify compounds and genetic pathways that modulate phenotypes associated with traumatic brain injury (TBI), which are also likely to be relevant to the treatment or prevention of traumatic brain injury in humans.

I. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

A "controlled impact," as used herein refers to an impact of sufficient force to cause traumatic brain injury (TBI) in a least a fraction of individuals, e.g., flies or worms subjected to the controlled impact.

An "effective amount," as used herein, means an amount of an agent sufficient to evoke a specified cellular or molecular effect according to the present invention.

An "impact-associated phenotype," as used herein, refers to a structural, functional, cellular, or molecular abnormality that occurs at any time point following an impact, which either does not occur in the absence of the impact, or occurs with less severity for a corresponding subject age.

"in vivo screening," as used herein, means assessing an outcome, e.g., a phenotype, cellular response, or a change in gene expression that occurs in a whole organism.

"Modulate" or "modulation," as used herein, mean increasing or decreasing a parameter relating to a phenotype of interest, e.g., modulating nerve regeneration.

"RNAi," as used herein refers to any of a number of methods or nucleic acid compositions that induce double-stranded RNA/DICER-mediated degradation of a target mRNA in living cells.

A "test agent," as used herein, refers to a molecule assessed for its ability to alter a specific phenotypic endpoint. Examples of test agents include, but are not limited to, (i) organic compounds of molecular weight less than about 600 daltons; (ii) nucleic acids; (iii) peptides (including stapled peptides); (iii) polypeptides; and (iv) antibodies.

"Traumatic Brain Injury," as used herein, refers to a closed-head injury to the brain of a vertebrate or invertebrate organism resulting from a collision.

II. Methods

Described herein are in vivo screening methods for identifying a candidate therapeutic agent for treatment or prevention of traumatic brain injury comprising the steps of: (i) subjecting one or more individuals of an invertebrate species having a brain to a controlled impact; (ii) dosing the one or more individuals with a test agent before or after the controlled impact; (iii) assessing an impact-associated phenotype in the one or more dosed individuals following the dosing and the controlled impact; and (iv) indicating that the therapeutic agent is a candidate therapeutic agent for treatment or prevention of traumatic brain injury if the impact-associated phenotype assessed in the one or more dosed individuals is reduced relative to the impact-associated phenotype assessed in individuals that have not been dosed with a test agent.

Suitable invertebrate species for use in the methods disclosed herein include species of the genus *Drosophila* (e.g., *Drosophila melanogaster*), and *C. elegans*, which have a brain and are highly amenable to genetic analysis and genetic perturbation, features that make them advantageous model organisms for use in the described screening assays. In other embodiments, *C. elegans* worms are used.

In some embodiments, *Drosophila* (e.g., *Drosophila melanogaster*) flies are used in the screening method. In some embodiments, the age range of the *Drosophila* flies to be used ranges from at least about one day to about 30 days, e.g., about 5 days, 7 days, 8 days, 10 days, 12 days, 15 days, 18 days, 20 days, 24 days, 26 days, or another age from at least about one day to about 30 days old. In some embodiments, the flies to be used are about 6 to about 10 days old. In other embodiments, the flies are at least 20 days old. In one embodiment, *Drosophila* larvae are used in the screening method.

A controlled impact used in the present methods can be administered using any of a number of approaches that afford an adjustable and reproducible impact velocity. In some embodiments, one or more individuals are enclosed in a container, and the container is then subjected to a controlled impact. In some cases, the controlled impact is administered by triggering a collision at a pre-determined velocity between the container and a strike surface that abruptly stops the container's motion. The container motion prior to the collision may be actuated in any of a number of ways. In some embodiments, the container is secured to a spring that is then deflected and released to produce an angular motion so as to trigger a controlled impact of the secured container with the strike surface (see, e.g., FIG. 1). One of ordinary skill in the art will appreciate that such a motion can be implemented using a number of devices, e.g., mechanical arm-counterweight systems, robotic arms, etc. . . . In other embodiments, the controlled impact is administered by dropping the container onto the strike surface from a height suitable on its own or in combination with other mechanical means, (e.g., a spring or motor) to impart a sufficient impact velocity to one or more containers enclosing individuals used in the method, e.g., *Drosophila* flies, *Drosophila* larvae, or *C elegans* worms. In some embodiments, a suitable impact velocity for the methods described herein is in the range of about 0.5 m/s to about 20 m/s, e.g., about 0.7 m/s, 0.8 m/s, 1.0 m/s, 1.2 m/s, 1.5 m/s, 1.7 m/s, 2.0 m/s, 2.5 m/s, 2.8 m/s, 3.5 m/s, 4.0 m/s, 4.5 m/s, 5.0 m/s, 6.0 m/s, 7.0 m/s, 8.0 m/s, 8.5 m/s, 9.0 m/s, 10 m/s, 12 m/s, 14 m/s, 15 m/s, 18 m/s, or another impact velocity from about 0.5 m/s to about 20 m/s. Where a controlled impact is to be administered based on dropping a container from a height alone, the height range needed to achieve an impact velocity from about 0.5 m/s to about 20 m/s is about 0.013 m to about 20.5 m. In some embodiments, where the container has a short axis and a long axis, the controlled impact with the strike surface is configured to occur along the long axis of the container. In other embodiments, the controlled impact is configured to occur along the short axis of the container.

In some embodiments, the timing and impact velocity of a controlled impact are implemented on a computer-controlled system, which, optionally, also stores information relating to the individuals subjected to a controlled impact, e.g., genetic background, test agents, age, etc.

In some embodiments, individuals may be subjected to multiple controlled impacts. In some embodiments, multiple controlled impacts include two to about ten controlled impacts, e.g., 3, 4, 5, 6, 7, 8, or 9 controlled impacts. In one embodiment, individuals are subjected to two controlled impacts. In another embodiment, individuals are subjected to three controlled impacts. In some embodiments, where multiple controlled impacts are administered, each subsequent controlled impact follows the previous one immediately (e.g., within a period of about 10 to about 30 seconds). In other embodiments, multiple controlled impacts are spaced out by an interval period of about one minute to about seven days, e.g., about 5 minutes, 10 minutes, 15 minutes, 20 minutes, 30 minutes, 45 minutes, 1 hour, 2 hours, 8 hours, 12 hours, 18 hours, 24 hours, 2 days, 3 days, 4 days, 5 days, 6 days, or another interval period from about one minute to about 7 days.

In some embodiments, multiple groups of individuals (e.g., a control group and a test agent group) are subjected to a controlled impact within a period ranging from 0 seconds to about 60 seconds, e.g., 10 seconds, 20 seconds, 30 seconds 40 seconds, 50 seconds or another interval from 0 seconds, or another interval from 0 seconds to about 60 seconds. In some embodiments, the multiple groups of individuals are subjected to a controlled impact simultaneously (i.e., within 0 seconds or a period substantially less than about one second). For example, the multiple groups may be placed in corresponding containers (e.g., at least two containers), which are then placed in a device configured to secure the multiple containers and administer a controlled impact to the multiple containers simultaneously. This is particularly useful to increase the throughput of the method where it is used for a large screen. In some embodiments, two groups to about ten groups of individuals are subjected to a controlled impact. In some embodiments, two groups of individuals are subjected to a controlled impact. In some embodiments, multiple containers include between 2 to 20 containers, e.g., 3, 4, 5, 6, 7, 8, 9, 10, 11, 12, 13, 14, 15, 16, 17, 18, 19, or 20 containers.

In some embodiments, where multiple groups are to be used in the method, each group in the multiple groups corresponds to a different genetic background, e.g., a different strain of flies, genetically modified flies expressing a transgene, flies harboring different mutations, etc. . . . . In other embodiments, each group within the multiple groups correspond to a different treatment group, e.g., an untreated group, a group treated with a different test agent, or group treated with a control agent In some embodiments, the controlled impact velocity is adjusted, so that eight strikes at the adjusted velocity produce a mortality rate of at least 40% in $w^{1118}$ flies at 24 hours post-injury.

In some embodiments, the individuals to be screened in the TBI method are administered a test agent before being subjected to a controlled impact. Such embodiments are particularly useful for identifying candidate prophylactic agents that reduce the level of an impact-associated phenotype when administered prior to an impact. The test agent may be administered to individuals used in the method from about 7 days to about 30 minutes prior to administration of the controlled impact, e.g., about 6 days, 5 days, 4 days, 3 days, 2 days, 1.5 days, 1 day, 18 hours, 12 hours, 7 hours, 6 hours, 5 hours, 4 hours, 3 hours, 2.5 hours, 1 hour, 45 minutes, 30 minutes, or another period from about 8 hours to about 15 minutes prior to the controlled impact being administered.

Test agents administered prior to a controlled impact would likely be most relevant as prophylactic agents for human subjects in the context of activities having a high risk of TBI, e.g., sports (e.g., boxing, football, karate) and combat. Alternatively, such prophylactic agents may also be useful within certain age groups that may have more severe consequences associated with TBI, as suggested by some of the results disclosed herein. Where the test agent is to be administered after the controlled impact, the test agent may be administered from about 30 minutes after the controlled impact to about 21 days after the controlled impact, e.g., about 45 minutes, 1 hours, 2 hours, 3 hours, 5 hours, 7 hours, 12 hours, 18 hours, 24 hours, 2 days, 3 days, 5 days, 7 days, 8 days, 10 days, 14 days, 16 days, 18 days, 3, or another period from about 30 minutes to about 21 days after the controlled impact.

Typically, invertebrates suitable for the methods described herein are dosed with a test agent by feeding. Alternatively, a test agent can be administered as an aerosol. Suitable concentrations of test compounds in food range from about 0.1 µM to about 100 mM for the purpose of a screen, e.g., about 0.2 µM, 0.5 µM, 1.0 µM, 10 µM, 50 µM, 0.1 mM, 1.0 mM, 1.5 mM, 2 mM, 3 mM, 5 mM, 7 mM, 8 mM, 20 mM, 30 mM, 50 mM, 70 mM or another screening concentration from about 0.1 µM to about 100 mM. Compounds can be administered once, multiple times, or continuously prior to or after the controlled impact. Those of ordinary skill in the art will appreciate that the precise timing, dosing, and route of test compound administration will be influenced by compound stability, compound toxicity and absorption, and the time course of the specific impact-associated phenotype to be assayed, e.g., lethality, innate immune system activation, or neurodegeneration.

The methods provided herein can be used to test previously identified drug candidates, or for new phenotypic screens of compound libraries. Compound libraries suitable for drug screening are available from a number of commercial sources. Examples of commercial sources for screening libraries include, but are not limited to, Microsource Discovery Systems, Inc. (Gaylordsville, Conn.); ChemBridge Corporation (San Diego, Calif.); and ChemDiv Inc. (San Diego, Calif.).

Impact-related phenotypes suitable for assessment in the methods described herein include, but are not limited to, lethality, an immune response (e.g., an innate immune response), neurodegeneration, a motor behavior deficit, changes in intestinal barrier permeability, a circadian abnormality, sleep abnormality, a learning deficit, a memory deficit, a social behavior deficit, changes in gene expression, microtubule structural changes, changes in enzymatic activity, changes in phosphorylation or other post-translational modifications, and changes in the concentration of small metabolites such as ATP or $Ca^{2+}$. Each of these endpoints has been associated with TBI in various studies. See, e.g., Harrison-Felix et al (2004), *NeuroRehabilitation,* 19(1):45-54; Helmy et al (2011), *Prog Neurobiol;* 95(3):352-372; Blennow et al (2012), *Neuron,* 76(5):886-899; Jang (2009), *NeuroRehabilitation;* 24(4):349-353; Castriotta et al (2011), *CNS Drugs,* 25(3):175-185; Millis et al (2001), *J Head Trauma Rehabil.;* 16(4):343-355; Hammond et al (2004), *J Head Trauma Rehabil.;* 19(4):314-328.

In some embodiments, the impact-associated phenotype to be assessed is lethality. Typically, the fraction of surviving individuals, e.g., flies, from a cohort is assessed after controlled impact starting from immediately after the impact up to about 60 days following the impact, e.g., 15 minutes, 30 minutes, 1 hours, 2 hours, 4 hours, 6 hours, 8 hours, 12 hours, 18 hours, 24 hours, 36 hours, 48 hours, 50 hours, 56 hours, 72 hours, 80 hours, 96 hours, 7 days, 10 days, 14 days, 21 days, 28 days, 35 days, 42 days, 45 days, 50 days, 55 days or another period from about 15 minutes to about 60 days following the controlled impact, or until all the flies being assessed have died.

Figure 6:
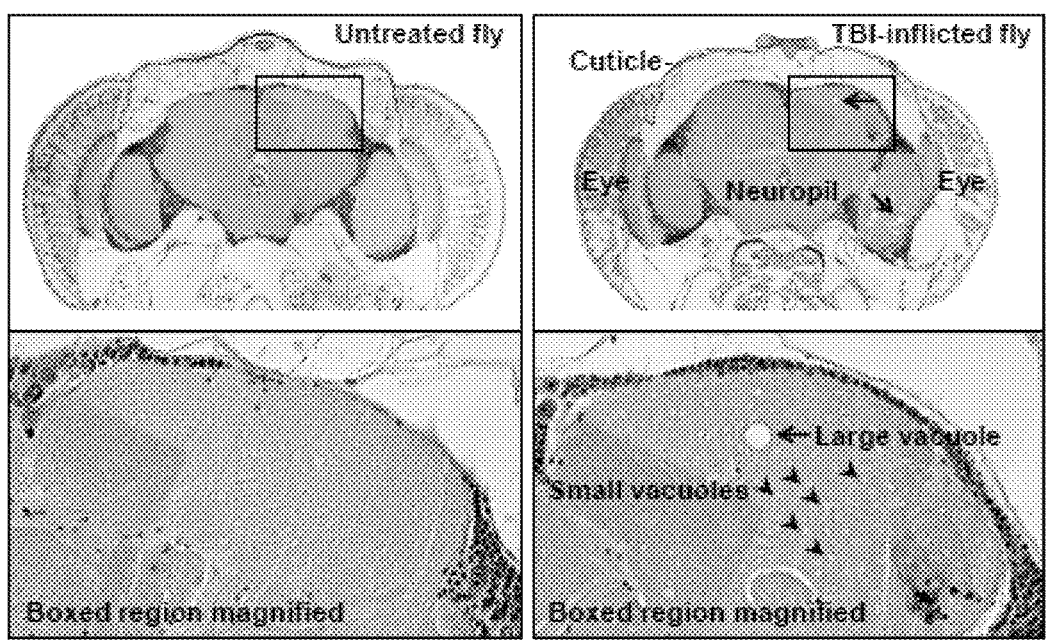
FIG. 6 shows photomicrographs of hematoxylin and eosin staining of coronal sections of fly brains 14 days following TBI, or of uninjured control fly brains. Vacuoles (indicated by arrows) are found throughout neuropil in flies subjected to TBI, but absent in control flies, demonstrate TBI-induced neurodegeneration. Diameter of fly head is 650 µm with vacuoles ranging in size from about 0.5 µm to about 10 µm.
Figure 7:
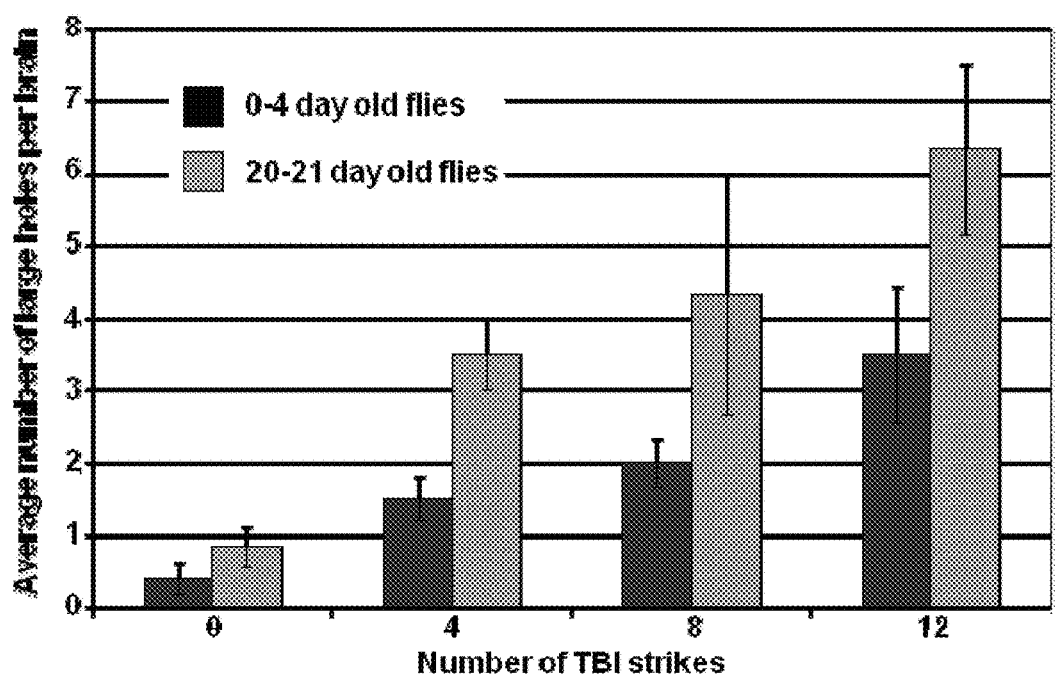
FIG. 7 shows a bar graph illustrating the relationship of age and number of controlled impacts versus the number of large vacuoles identified in fly brains 14 days after inducing TBI. Increasing neurodegeneration, as indicated by large vacuole (hole) number, is observed with increasing age or controlled impact number.

In other embodiments, the impact-associated phenotype assessed is neurodegeneration. In some embodiments, where *Drosophila* flies are subjected to a controlled impact, neurodegeneration is assessed by examining the brain morphology in surviving flies at various time points following impact. The formation of vacuolar-like lesions in the brain neuropil is commonly observed in fly models of human neurodegenerative disorders. The neuropil is composed of neuron axons, synaptic terminals, and ensheathing and astrocyte-like glial cells. In one embodiment, vacuolization is assessed by hematoxylin and eosin staining of thin paraffin sections of fly brain neuropil, followed by counting or estimating number of vacuoles of a threshold size per brain. As disclosed herein, brain sections from uninjured fly neuropils have a uniform appearance, whereas flies analyzed 14 days after the standard TBI protocol, detailed infra, contain neuropils with numerous small vacuoles and a few large vacuoles (FIG. 6) the number of which is influenced by the number of controlled impacts and age (FIG. 7). In some embodiments, neurodegeneration is assessed from about 5 days to about 60 days from administration of a controlled impact, e.g., 6 days, 7 days, 8 days, 10 days, 12 days, 14 days, 16 days, 18 days, 20 days, 25 days, 30 days, 40 days, 45 days, 50 days or another time point from about 5 days to about 60 days from administration of the controlled impact.

Figure 8:
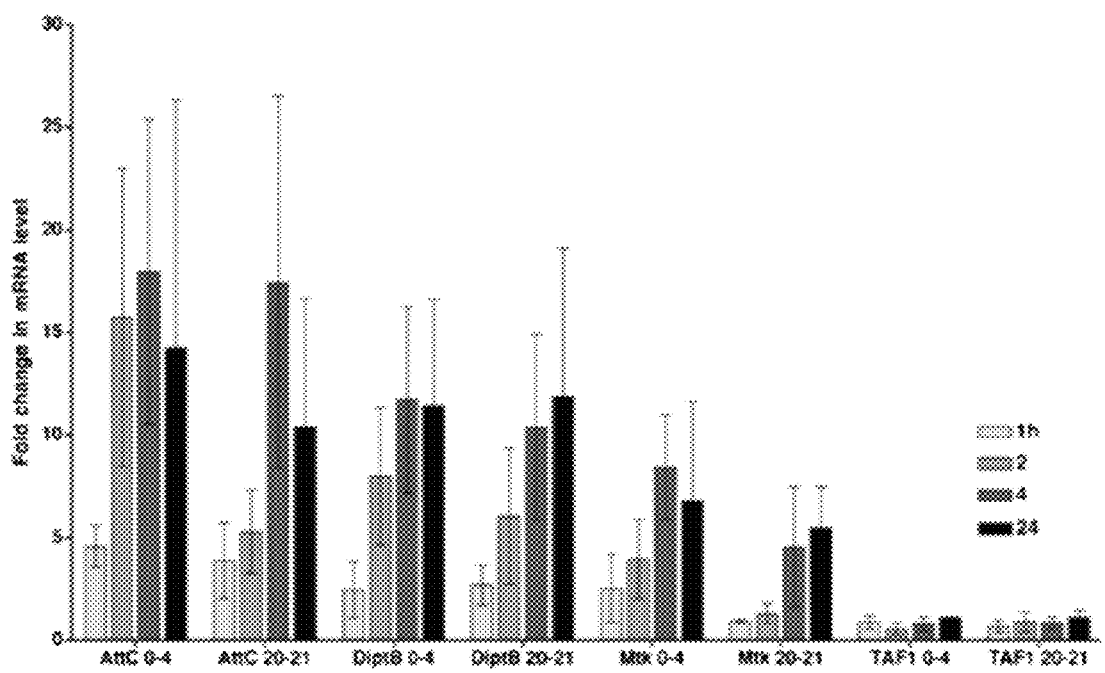
FIG. 8 shows bar graphs illustrating the fold-increase in mRNA levels in flies subjected to a TBI protocol versus untreated flies at the indicated time points after treatment of 0 to 4 or 20 to 21-d-old flies. The AMP genes examined were Attacin-C (AttC), Diptericin B (DiptB), and Metchnikowin (Mtk), and the control gene examined was TBP-associated factor 1 (TAF1). Error bars indicate the SEM for at least three independent trials.

In other embodiments, the impact-associated phenotype assessed is an immune response. In one embodiment, where *Drosophila* flies are used, an innate immune response is assessed at various time points in groups of individual flies following the controlled impact. Flies have two evolutionarily conserved innate immune response signaling pathways that lead to the production of antimicrobial peptides (AMPs) such as Attacin C and Metchnikowin. The Toll pathway primarily responds to eukaryotic pathogens and gram-positive bacteria. In contrast, the Immune deficiency (Imd) pathway, which is analogous to the mammalian TNF pathway, primarily responds to gram-negative bacteria. Excess or prolonged activation of either pathway independently of pathogen infection can cause neurodegeneration (see, e.g., Petersen et al (2010), *Fly,* 6:169-172). As disclosed herein, activation of the innate immune response is also an immediate and long-term reaction to TBI in flies. qPCR analysis showed that a controlled impact in flies results in an immediate and prolonged increase in the expression of AMP genes (FIG. 8). Thus, in one embodiment, an increase in AMP gene expression, at the mRNA level especially, is assessed as an impact-associated phenotype. This assessment can be made by any of a number of well-known methods in the art, e.g., Northern blot analysis, RNase protection, qRT-PCR, and in situ hybridization. Alternatively, changes in AMP gene expression can be monitored indirectly by the use of transgenic reporter lines as described in, e.g., Tzou et al (2000), *Immunity,* 13:737-748. For example, the transgenic reporter line may express a fluorescent reporter protein. Furthermore, the level of expression of AMP genes varies with injury severity and the recovery time between injuries. In some embodiments, an innate immune response is assessed from about 30 minutes to about 60 days following administration of a controlled impact, e.g., 1 hour, 2 hours, 3 hours, 4 hours, 7 hours, 12 hours, 18 hours, 24 hours, 36 hours, 48 hours, 3 days, 5 days, 7 days, 14 days, 21 days, 30 days, 40 days, 45 days, 50 days, 55 days or other time points from about 30 minutes to about 60 days following administration of the controlled impact.

In other embodiments, where *Drosophila* flies are utilized in the method, sleep, circadian rhythms, motor activity, or a combination thereof are assayed in flies after being subjected to a controlled impact, and are assessed for changes in these endpoints relative to control flies that are not subjected to a controlled impact. Methods for assessing sleep (rest), motor activity, and circadian rhythms in *Drosophila* are known in the art, as described in, e.g., Bushley et al (2011), *Int Rev Neurobiol*, 99: 213-244. Gilestro (2012), *Nat Protoc.*; 26; 7(5):995-1007; Zordan et al (2007), *Methods Mol Biol*, 362:67-81; and Nichols et al, *J Vis Exp.*, 7; (61). pii: 3795.

In further embodiments, where *Drosophila* flies are used, learning, memory, or social behavior deficits are determined after being subjected to a controlled impact. Exemplary learning and memory assays in *Drosophila* include, but are not limited to, olfactory-conditioning as described in, e.g., Murakami al (2010), *J Neurosci Methods*, 188(2):195-204. Assays of social behavior in *Drosophila* are also known in the art, as exemplified in Simon et al (2012), *Genes Brain Behav*, 11(2): 243-252; Dankert et al (2009), *Nat Methods*, 6(4): 297-303.

Also described herein is (i) subjecting one or more individuals of an invertebrate species having a brain to a controlled impact, wherein the individuals comprise a transgene; (ii) expressing the transgene in the one or more individuals before or after the controlled impact; (iii) assessing an impact-associated phenotype in the one or more individuals following expression of the transgene and the controlled impact; and (iv) indicating that the transgene modulates the impact-associated phenotype if the impact-associated phenotype assessed in the one or more dosed individuals is reduced relative to the impact-associated phenotype assessed in individuals that do not express the transgene.

Production of transgenic *Drosophila* and *C. elegans* lines and their progeny are established in the art as described in, e.g., Dahmann (2008), *Drosophila: Methods and Protocols (Methods in Molecular Biology)*, Humana Press; and *WormBook*, ed. The *C. elegans* Research Community, WormBook, doi/10.1895/wormbook.1.7.1, online as wormbook.org.

In some cases, transgene expression is tissue-, cell type-, or tissue region-selective. In some embodiments, where *Drosophila* flies are used, the transgenic flies will comprise a tissue-selective-Gal4 expression cassette. In other embodiments, the expression cassette will drive ubiquitous transgene expression. Useful transgene expression cassettes in these embodiments include, but are not limited to, C155-Gal4, Repo-Gal4, Actin-Gal4, TH-Gal4, and OK107-Gal4. In other embodiments, the transgene to be expressed can be inducibly expressed such that expression is under temporal control, and can be induced before or after a controlled impact used in the above-mentioned screening method. Such inducible transgene expression systems are known in the art as described in, e.g., McGuire et al (2004), *Trends Genet.* 20(8):384-391.

In some embodiments a transgene to be expressed comprises the open reading frame for a polypeptide. For example, the transgene may encode a polypeptide associated with a neurodegenerative disease, which is particularly relevant in view of literature pointing to a link between TBI and an increased likelihood of neurodegenerative disease (see, e.g., Shively et al (2012), *Arch Neurol*, 69(10):1245-1251. In some embodiments, the polypeptide associated with a neurodegenerative disease comprises the amino acid sequence of hAPP, hAbeta1-42, a hTau, a hSynuclein, hHuntingtin, a hTDP-43, a hSOD, hLRRK2, a hGSK3β, a polyQ polypeptide comprising a at least 35 contiguous glutamines, or any combination thereof. Nucleotide sequences for such genes are found in publicly available databases, e.g., GenBank with the following Accession Nos.:hAPP (GenBank 1.NM_000484.3); hTau (NM_001123066.6), hsynuclein (NM_000345.3), hhuntingtin (NM_002111.6), hTDP-43 (NM_007375.3), hFUS/TLS (NM_004960.3), hSOD1 (NM_000454.4), hGSK3β (NM_002093.3), and hLRRK2 (NM_198578.3).

In other embodiments, the transgene includes a gene for a non-coding RNA, e.g., non-coding RNAs or untranslated portions (5' or 3' UTR) portions of coding RNA that include at least 40 repeat motifs, e.g., CTG, CCTG, CAG, ATTCT. See, e.g., Todd et al (2010), *Ann Neurol*, 67(3): 291-300.

In other embodiments, the transgene encodes an RNAi. For example, a systematic reverse genetic screen can be implemented in *Drosophila* flies using a genome-wide RNAi library to generate many transgenic RNAi fly lines, as described in, e.g., Dietzl et al (2007), *Nature*, 448(7150): 151-156. As discussed above for polypeptide-encoding transgenes, multiple expression systems are known for spatial and temporal control of RNAi knock-down of RNAi-targeted genes. In further embodiments, the transgene to be expressed encodes a microRNA.

Also described herein is a method for identifying an invertebrate mutant carrying a modifier mutation that modifies an impact-associated phenotype, comprising: (i) subjecting one or more mutants of an invertebrate species having a brain to a controlled impact, wherein the one or more mutants are from a mutant line carrying at least one mutation relative to a control line; (ii) assessing an impact-associated phenotype in the one or more mutants; and (iii) indicating that the mutant line carries a mutation that modifies an impact-associated phenotype if the impact-associated phenotype assessed in the mutant is attenuated or enhanced relative to the impact-associated phenotype assessed in a control line.

In some embodiments the mutant lines to be screened in the method are randomly mutagenized mutant lines, e.g., lines that were generated by transposon-based mutagenesis (e.g., P-element mutagenesis) or chemical mutagenesis (e.g., with ethyl methanesulfonate).

In some embodiments the method also includes mapping a modifier mutation in a mutant line identified by the above-mentioned method. In other embodiments, modifier mutations are identified and mapped in natural fly populations or in the *Drosophila* Genetic Reference Panel strains as described in Mackay et al (2012), *Nature*, 482(7384):173-178.

III. Systems and Devices

Also described herein are systems and devices for implementing the disclosed screening assays.

Accordingly, disclosed herein is a controlled impact trauma (CIT) system comprising: (i) a base; (ii) a deceleration assembly comprising a strike surface; (iii) an adaptor assembly holding one or more containers for containing a plurality of individuals of an invertebrate species having a brain; and (iv) an acceleration assembly coupled between the base and the adaptor assembly, and configured to accelerate the one or more containers held in the adaptor assembly toward the strike surface to generate a controlled impact of the one or more containers on the strike surface at a predetermined, adjustable velocity. Also described herein is a CIT device comprising: (i) a base; (ii) a deceleration assembly comprising a strike surface; (iii) an adaptor assembly configured to hold at least one container of dimensions suitable to contain a plurality of viable *Drosophila* flies; and (iv) an acceleration assembly coupled between the base and the adaptor assembly, and configured to accelerate, when in use, the one or more containers held in the adaptor assembly toward the strike surface to generate a controlled impact of at least one container on the strike surface at a predetermined, adjustable velocity. An exemplary, non-limiting embodiment of such a CIT device is illustrated in FIG. 1.

In some embodiments, the CIT system or device is configured for use with one or more containers of dimensions suitable to contain about 1 to about 100 *Drosophila* flies. In other embodiments, the CIT system is configured to hold containers of dimensions suitable for about 1 to 100 *C. elegans* worms. In some embodiments, the adaptor assembly in the CIT system or device is configured to hold at least two containers containing the individuals, e.g., separate groups of *Drosophila* flies with different characteristics such as test agent exposure, genetic background, age, etc. In other embodiments, the adaptor assembly can hold from 2 to 10 containers, which can be subjected to impact simultaneously using the CIT system or device, and is particularly useful for increasing the throughput of the TBI screening methods disclosed herein. Preferably, containers used in the CIT system or device are transparent. In some embodiments, a container is made of plastic. In other embodiments, a container is made of impact-resistant glass.

In some embodiments, a container in the CIT system or device is labeled with a digital data tag in the form of a label (e.g., a label having a 1D or 2D bar code) that is readable by a scanning device. Such data tags may encode a number of data useful for the TBI screening methods described herein, e.g., characteristics of individuals in the container such as genetic background, age, test agent dosing regimen, etc. In some embodiments, the data tag is a radio frequency identification (RFID) tag, which is particularly useful in tracking individual containers of individuals, e.g., a group of flies in the context of a screen. In some embodiments, the RFID tag is a two way RFID tag, which also allows modification or addition of data on the tag, which can be useful for storing or modifying data on the tag, especially after the CIT system or device is used to provide a controlled impact to a tagged container. For example, the actual impact velocity, time of day, date, etc. can be recorded on the tag and read out later. RFID tags are commercially available from other sources, e.g., Symbol (Matrics) Read/Write Passive RFID Tags from Asentrix, Inc. (Seattle, Wash.), In some embodiments, the deceleration strike surface in the CIT system or device contains a material such as rubber so as to somewhat attenuate impact force of a container upon impact. In general, materials of suitable stiffness, have a young's modulus no greater than about 2 GPa. In some embodiments, the strike surface contains rubber.

In some embodiments, the acceleration assembly includes a spring, which, once deflected to a specified position and released, provides the kinetic force to accelerate the CIT system or device container to a suitable impact velocity. In other embodiments the acceleration assembly includes an electric motor that permits an adjustable kinetic force to accelerate the container. In other embodiments, the CIT system or device may be configured to accelerate a container to a suitable impact velocity by releasing the container from a sufficient height, or by a combination of height and additional kinetic energy imparted by a spring or motor. For example, the height range needed to achieve an impact velocity from about 0.5 m/s to about 20 m/s is about 0.013 m to about 5.2 m.

In some embodiments, the CIT system or device is configured to provide an adjustable predetermined impact velocity of about 5 m/s to about 20 m/s to the one or more containers, e.g., about 7 m/s, 8 m/s, 10 m/s, 12 m/s, 15 m/s, 17 m/s, or another impact velocity from at least about 5 m/s to about 20 m/s.

In some embodiments, the individuals held in the CIT system are dosed with a test agent, e.g., as part of a screen designed to identify agents that reduce the effects of TBI as described herein.

Optionally, a CIT system may include a computer system and a digital to analog interface that permits a user to specify various parameters of the CIT system, e.g., predetermined container impact velocity, number of impacts to be administered, and interval between impacts. The computer system may also include a data storage system, which can be used to establish a screening database that includes information such as test agent characteristics, genetic background of individuals tested, impact velocity, number of impacts time of day, date, etc.

The invention will be more fully understood upon consideration of the following non-limiting Examples.

EXAMPLES

Example 1 an Exemplary Controlled Impact Trauma (CIT) Device

As shown in FIG. 1, we constructed a simple CIT device. This device consists of a metal spring, which serves an "acceleration assembly," labeled (5) in FIG. 1, that is clamped at one end to a wooden board "base" (1) and has the free end positioned over a hard rubber pad "strike surface" (2). A standard plastic vial ("container" (4)) containing unanesthetized flies is connected to the free end "adaptor assembly" (3) of the spring. The flies are confined to the bottom quarter of the vial by a stationary cotton ball. When the spring is deflected and released, the vial impacts the hard rubber pad, and a mechanical force is delivered to the flies as they contact the vial wall. Individual flies presumably contact the wall with different regions of their head and/or body and with different forces, so primary injuries will vary among flies in the same vial. The lack of penetrating injuries and the randomness of impact location and strength are features of closed head TBI in the human population.

Example 2 Repeated TBI Affects Survival Over Time

Figure 2:
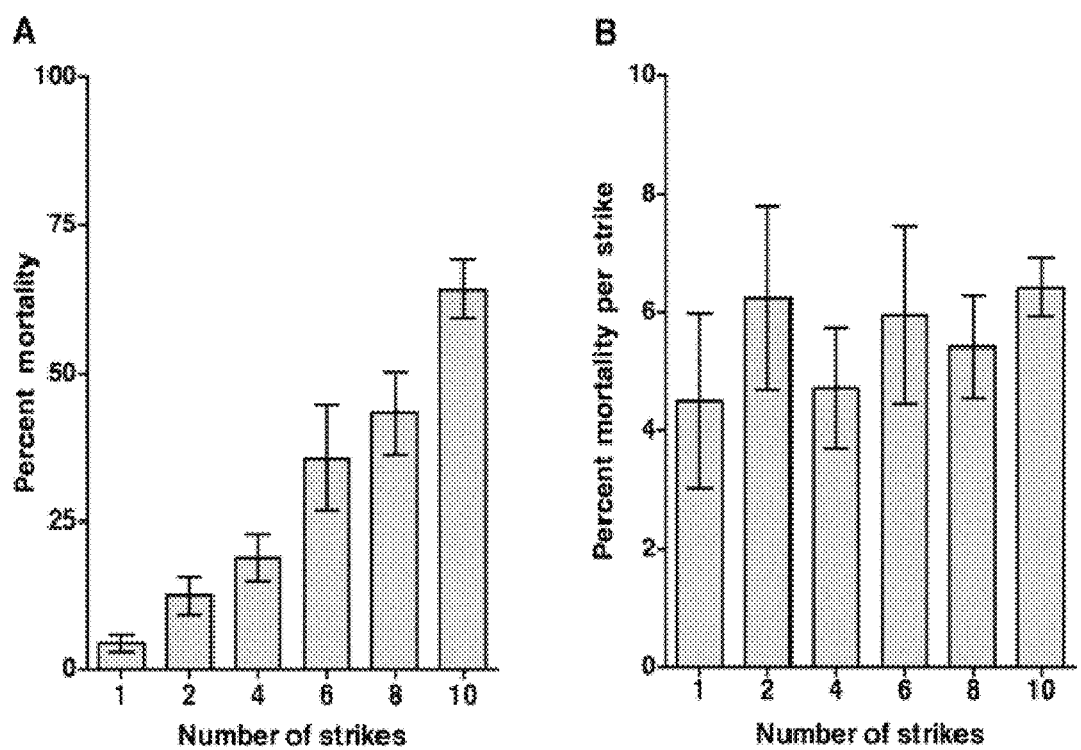
FIG. 2 shows a line graph illustrating the effect of the number of strikes on mortality of a population of *Drosophila* flies at 24 h following a varying number of controlled impacts using the CIT device described in FIG. 1. Impacts were separated by five minute intervals. (A) Graphed is the number of strikes versus the percent mortality within 24 h. Percent mortality values were normalized to those of untreated flies. (B) Data from panel A are graphed as the percent mortality per strike. The number of strikes did not significantly affect the percent mortality per strike (P=0.82, one-way ANOVA)

To determine whether repetitive primary injuries affect the frequency of mortality in the short-term, we varied the number of strikes flies received and measured the percentage of flies that died within 24 h. To minimize any variation in outcome associated with differences in age, genotype, or gender, we used 0-3-day old $w^{1118}$ flies in every experiment, with an approximately equal number of males and females. Flies received 0-10 strikes with the spring deflected to 90° and with 5 min recovery periods between strikes. After a single strike, 4.5±1.2% of the flies died within 24 h (FIG. 2A). Additional strikes resulted in an increased percentage of flies that died; however, additional strikes did not increase the percentage of flies that died per strike (FIG. 2B). The fact that not all flies died after a single strike indicates that primary injuries cause death in the short-term only if they exceed a specific threshold, where threshold is presumably a composite measure of impact location and strength. Furthermore, the fact that the percentage of flies that died per strike was not affected by the number of strikes indicates that primary injuries below the threshold do not make flies more susceptible to death in the short-term from receiving additional primary injuries. These data were also published in Katzenberger et al (2013), *Proc. Natl Acad. Sci. USA*, 110(44):E4152-4159.

Example 3 The Lethality of TBI in *Drosophila* is Age-Dependent

Based on the data described in Example 2, we designed a standard TBI protocol for administering controlled impacts to generate primary injuries. The standard TBI protocol consisted of four impacts with five min recovery intervals between impacts. Reproducibility and rapidity were the driving forces behind the choice of protocol parameters. Additionally, the standard TBI protocol resulted in moderate mortality within 24 h that could be subject to suppression or enhancement by genetic and environmental factors that affect primary injuries.

Figure 3:
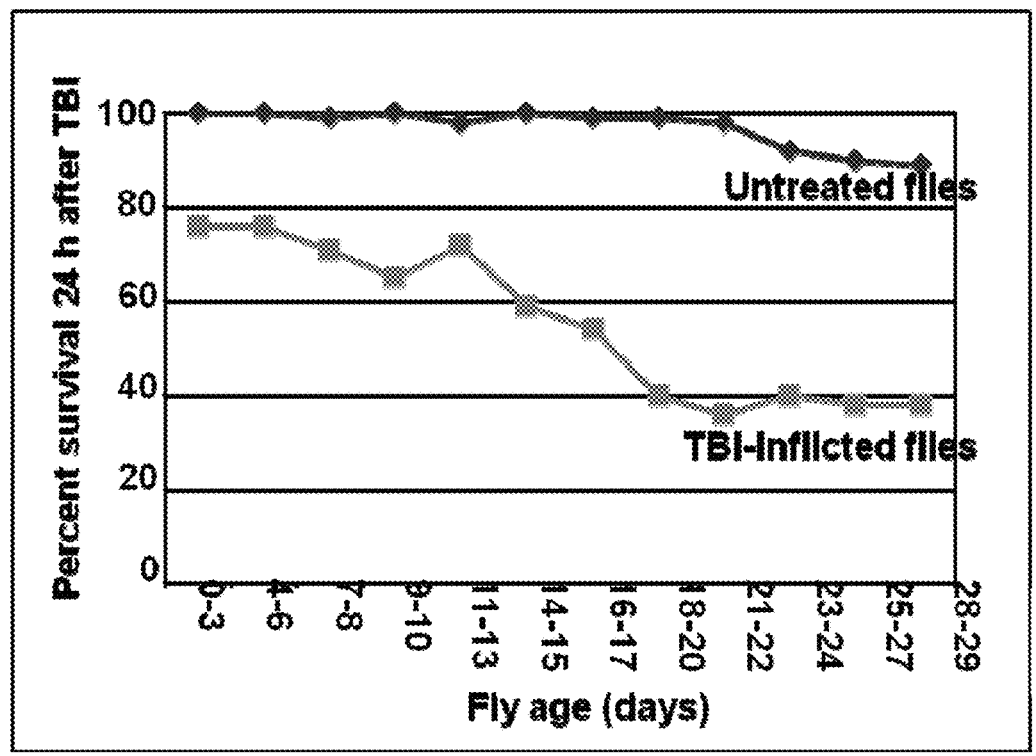
FIG. 3 shows a line graph illustrating the effect of age on fly survival at 24 hours following TBI.

The standard TBI protocol was used to determine the effect of gender and age on mortality in the short-term. $w^{1118}$ male and female flies that were 0-4 or 20-22 days old were assayed separately for death within 24 h. Gender did not have a significant effect on mortality at either age. In contrast, as shown in FIG. 3, age did have a significant effect on mortality. For both male and female flies, mortality was approximately two-times higher in older flies than younger flies.

To examine the effect of age more systematically, flies in 12 age groups ranging from 0-3 to 28-29 days old were treated with the standard TBI protocol and scored for the percent mortality within 24 h. The data revealed an increase in percent mortality as age increased (FIG. 3). These results suggest that cellular and molecular changes occur during aging that lower the primary injury threshold for death in the short-term.

Example 4 Mortality Caused by TBI is Strongly Influenced by Genetic Background

Figure 4:
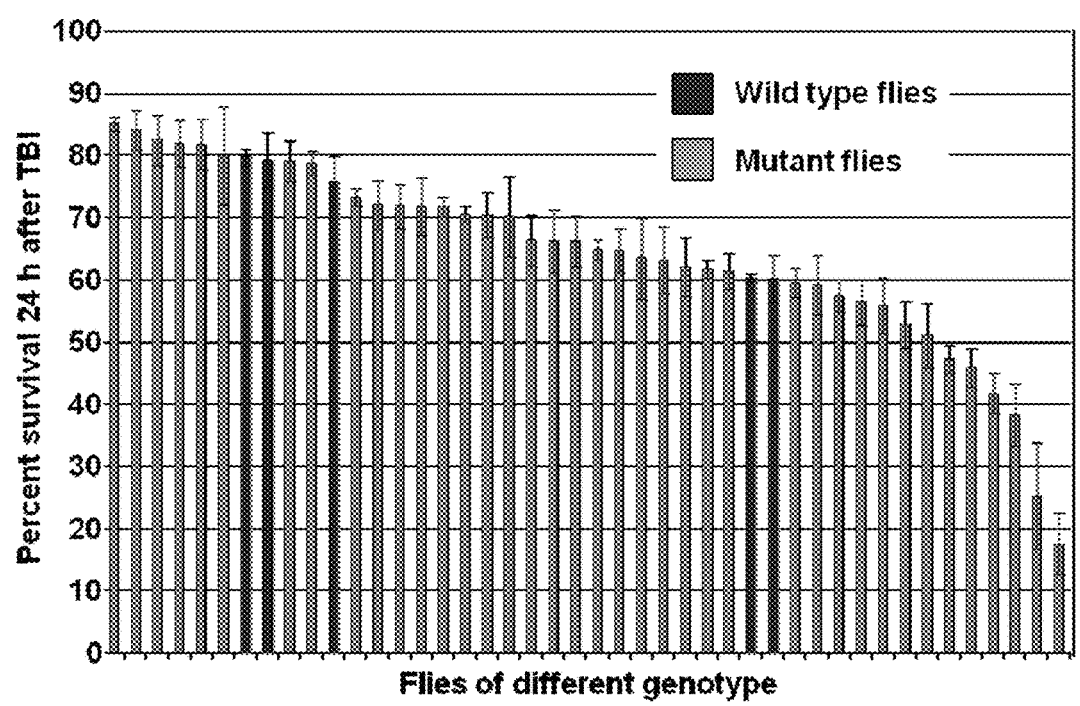
FIG. 4 shows a bar graph illustrating the influence of varied genetic backgrounds on fly survival 24 hours following TBI.
Figure 9:
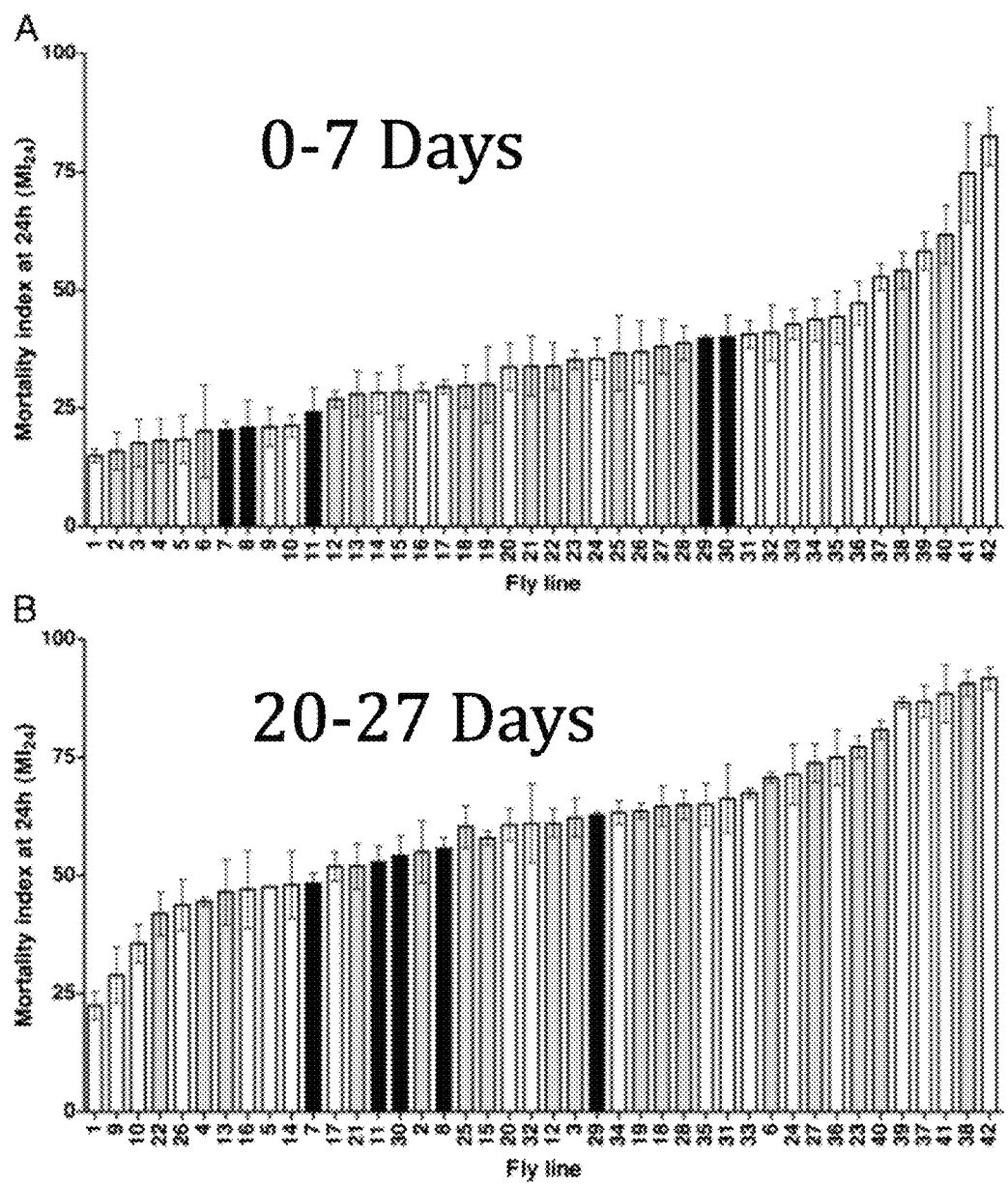
FIG. 9 The 24 hour mortality index (MI24) is strongly affected by genetic background and age. Histograms show the MI24 for 42 different fly lines treated with the standard TBI protocol and tested in flies (A) 0-7 days and (B) 20-27 days old. The MI24 vs. fly genotype is graphed. MI24 values were normalized to those of untreated flies. Genotypes are listed in Table 1. White bars indicate fly lines containing mutations in genes implicated in the Imd pathway. Gray bars indicate fly lines containing mutations in genes implicated in the Toll pathway. Black bars indicate fly lines commonly used as wild-type controls in *Drosophila* experiments. For reference, fly line number 7 is w1118. Error bars indicate the SD for at least three independent trials of 60 flies each. Note that the data in (A) are replotted from FIG. 4 using a "mortality index" rather than "percent survival."

To determine the extent to which genetic background modulates the primary injury threshold, we examined 42 fly strains listed in Table 1 and corresponding to those shown in FIGS. 4 and 9.

TABLE 1

Fly Strains shown in FIG. 4
(left to right)

1. $key^{f05097}$
2. $spz^3$/TM1
3. $nec^2$/CyO
4. $cact^4$/CyO
5. $GNBP^{e3371}$
6. $tub^{e03259}$
7. $w^{1118}$
8. Oregon-R-C
9. $Imd^{SDK}$
10. $key^{c0283}$
11. Canton-S
12. $Irc^{MB11278}$
13. $Iap2^{G2326}$
14. $Dredd^{EY08404}$
15. $spz^2$/TM1
16. $Tak1^{179}$
17. $PGRP-LC^{BG00650}$
18. $dl^4$/CyO
19. $pit^{EY10870}$
20. $Tab2^{201Y}$ TABLE 1-continued Fly Strains shown in FIG. 4
(left to right)

21. $Duox^{KG07745}$
22. $Dif^1$
23. $Myd88^{KG03447}$
24. $pit^{f06954}$
25. $pll^7$/TM3
26. $Dredd^{EP1412}$
27. $nec^{10}$/CyO
28. $pll^2$/TM3
29. $cn^1 bw^1$
30. $y^1 w^1$
31. $pirk^{EY00723}$
32. $Imd^{10191}$
33. $ird5^{EY02434}$
34. $ird5^{KG08072}$
35. $Tab2^{EY00723}$
36. $PGRP-LC^{Delta5}$
37. $Rel^{E20}$
38. $tub^2$/TM8
39. $Rel^{E38}$
40. $Dif^2$
41. $Tak1^2$
42. PGRP-L Five strains (shown in bold in Table 1) are commonly used as wild type controls in fly experiments and 37 strains contained mutations in genes that encode components of the Imd or Toll pathway. We treated flies of 0-7 days old with the standard TBI protocol and assayed mortality within 24 hours. As shown in FIG. 4, the percent mortality within 24 h after injury showed wide variation among strains, ranging from 14.9±1.2% to 82.5±5.0%. Variability was even observed among wild type controls, for which the percent mortality ranged from 20.3±1.4% to 39.9±3.8%. Among the mutant lines there were striking differences for different alleles of the same gene. For example, the percent mortality for $Imd^{SDK}$ and $Imd^{10191}$ was 21.0±3.3% and 40.9±4.8%, respectively. Additionally, the percent mortality did not correlate with either the Imd or the Toll pathway. For example, mutations in Relish, which encodes the NF-κB transcription factor in the Imd pathway, had a significantly different effect on the percent mortality than mutations in Kenny, which encodes an activator of Relish ($Rel^{E20}$, 47.2±2.3%; $Rel^{E38}$, 41.7±3.3%; $Key^{f05097}$, 8.5±1.2%; and $Key^{c02831}$, 7.9±1.9%). These data suggest that in young flies many genes in the genetic background underlie the heterogeneity in the primary injury threshold for death in the short-term.

In a follow-up experiment, the interaction of age and genetic background on TBI-induced mortality was assessed. Interestingly, the relative susceptibility of various strains to TBI-induced mortality also appeared to be age-dependent (FIG. 9). Thus, not only was there an overall increase in sensitivity to TBI-induced mortality with increased age, but in some cases there were also changes in the ranking of sensitivity among lines (e.g., sensitivity of lines 2 and 10 at 0-7 days of age versus 20-27 days of age). Thus, it appears that different genetic influences contribute to TBI-sensitivity in an age-dependent manner.

Figure 10:
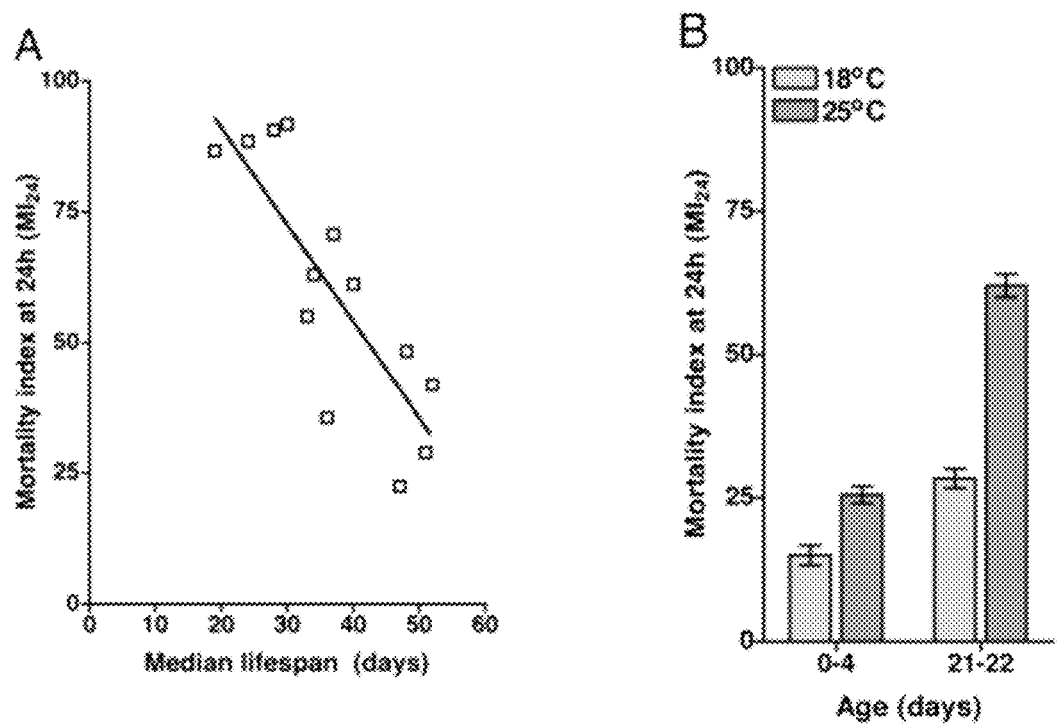
FIG. 10 The susceptibility of different fly lines to TBI-induced mortality is inversely correlated with their respective longevity. (A) The MI24 of 20- to 27-day-old flies is graphed vs. the median lifespan for 14 of the fly lines that were analyzed in FIG. 9. The lines that were analyzed are listed in Table 1. RelE20 and RelE38 flies had the same MI24 and median lifespan, so they appear as a single open box on the graph. (B) The MI24 is graphed for w1118 flies of the indicated age that were raised at either 18° C. or 25° C. MI24 values were normalized to those of untreated flies. Temperature had a significant effect on the MI24 for both 0- to 4-day-old flies (P=0.012, one-tailed t test) and 21- to 22-day-old flies (P=0.001, one-tailed t test). Error bars indicate the SD for at least three independent trials of 60 flies each.

Because the primary injury threshold varies with age, we examined the correlation between MI24 and longevity in the absence of TBI. We analyzed 14 fly lines, including lines with low, average, or high MI24 after treatment with the standard TBI protocol. We found a negative linear relationship between the MI24 and the median lifespan for both 0- to 7-day-old and 20- to 27-day-old flies (FIG. 10A). The correlation coefficient r between the MI24 and the median lifespan was −0.67 for 0- to 7 day-old flies and −0.84 for 20- to 27-day-old flies. Thus, the longevity of a particular fly line and its primary injury threshold for death within 24 hours appeared to be largely determined by the same genetic factors. To test this proposition, we extended the lifespan of flies and examined the effect on the MI24. To extend the lifespan, we raised flies at 18° C. rather than at 25° C., the temperature at which flies were raised for all of the prior experiments. $w^{1118}$ flies raised at 18° C. had a significantly longer median lifespan than flies raised at 25° C. (68.5±0.8 d vs. 48.3±1.2 d, P<0.0001, one-tailed t test). After treatment with the standard TBI protocol, $w^{1118}$ flies raised at 18° C. had a significantly lower MI24 than equivalent-age flies raised at 25° C. (FIG. 10B). The negative correlation between natural longevity and MI24 was observed for both 0- to 3-d-old and 21- to 22-day-old flies. Thus, flies of the same genotype and chronological age but different median lifespan differed in their primary injury threshold for death within 24 hours. This result indicates that environmental factors such as temperature determine both the longevity of a particular line in the absence of injury and its primary injury threshold for death within 24 hours.

Figure 5:
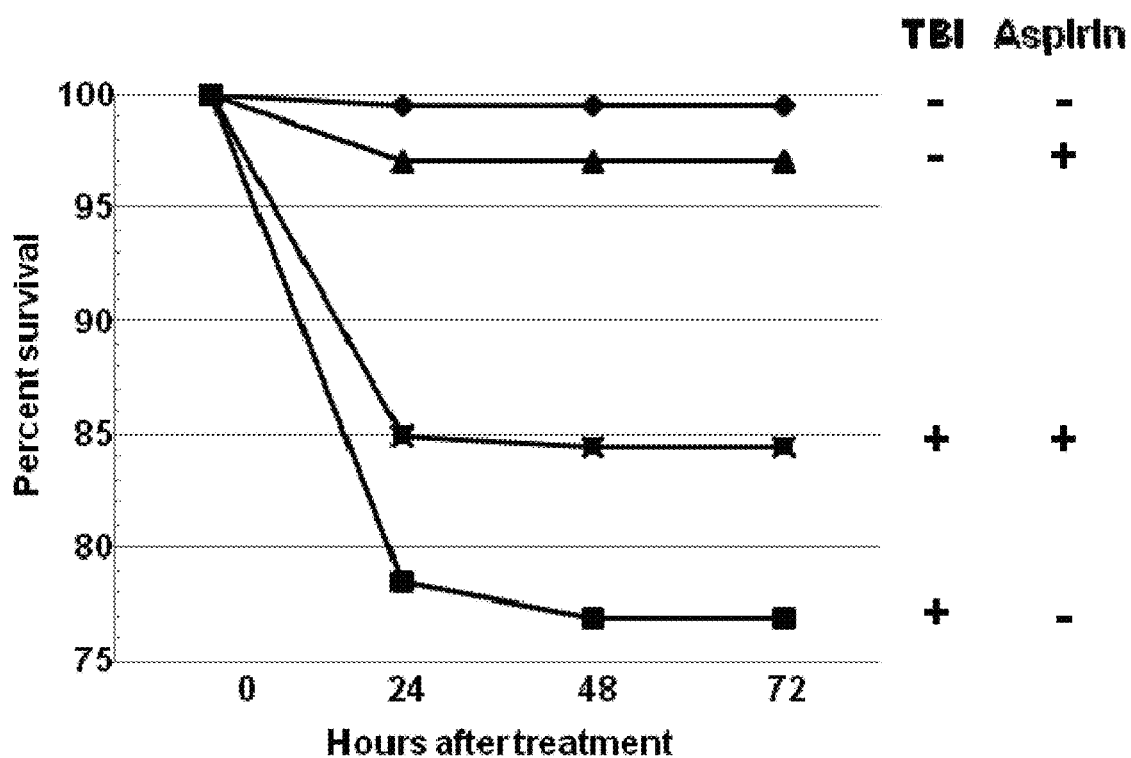
FIG. 5 shows a line graph illustrating the ability of aspirin to increase fly survival at various time points following TBI. Flies were treated with aspirin for 4 days prior to TBI.

Example 5 Mortality Caused by TBI in Drosophila can be Reduced by a Pharmacological Intervention As a proof of concept for identifying an agent that could reduce the severity of an impact-associated phenotype, e.g., lethality, we tested whether the non-steroidal anti-inflammatory drug, aspirin, affects TBI outcomes. Flies were treated with aspirin by feeding and then subjected to the standard TBI protocol. 0.4 ml of aspirin (200 mg/ml in DMSO) or DMSO only was added to vials with food and allowed to absorb into the food for two hours. 0-3-day old $w^{1118}$ flies, with an approximately equal number of male and female flies, were cultured on the food for four days. Flies were then left untreated or subjected to the standard TBI protocol. As shown in FIG. 5, 24 hours after a controlled impact, aspirin-treated flies had lower mortality than the DMSO-treated flies. Thus, aspirin pre-treatment raises the primary injury threshold.

Example 6 TBI Triggers Neurodegeneration in Drosophila

TBI is associated with neurodegeneration, e.g., Chronic Traumatic Encephalopathy (CTE), in humans: To determine if neurodegeneration is also a long-term outcome of TBI in flies, we analyzed the morphology of fly brains following a controlled impact administered with the device described in Example 1. The formation of vacuolar-like lesions in the brain neuropil is commonly observed in fly models of human neurodegenerative disorders. The neuropil is composed of neuron axons, synaptic terminals, and ensheathing and astrocyte-like glial cells. Hematoxylin and eosin staining of thin paraffin sections of uninjured fly neuropils revealed a uniform appearance as shown in FIG. 6. In contrast, as shown in FIG. 6, flies analyzed 14 days after the standard TBI protocol contained neuropils with numerous small vacuoles and a few large vacuoles. Thus, TBI in Drosophila, as is the case for humans, triggers progressive neurodegeneration.

Example 7 TBI-Induced Neurodegeneration in Drosophila is Age-Dependent

We further examined neurodegeneration in flies as a function of the number of impacts, and as a function of age.

As shown in FIG. 7, with an increasing number of impacts, an increasing number of large vacuoles was observed in neuropil. Also, large vacuoles occurred more frequently in experiments performed on older flies (20-21 days old) than on younger flies (1-4 days old). These data indicate that secondary injuries cause neurodegeneration and that cellular and molecular events that occur during aging enhance the secondary injuries that cause neurodegeneration.

Example 8 TBI Triggers an Innate Immune System Response in Drosophila

One of the consequences associated with TBI is inflammation, which is mediated by activation of the innate immune system. Thus, we sought to determine if the innate immune system is similarly activated following TBI in Drosophila. In this experiment, flies were treated with the standard TBI protocol (4 strikes with 5 minutes between strikes). Each experimental time point involved 60 $w^{1118}$ flies. Total RNA was isolated from fly heads and quantitative PCR (reverse transcription-real time PCR) was used to determine the expression of the innate immune response genes Attacin C and Metchnikowin. Gene expression levels were normalized to actin levels and fold changes were determined relative to flies that were untreated (Control). As shown in FIG. 8, both of these AMP genes exhibited a rapid induction of expression, which was elevated above control levels out to the latest time point examined (72 hours). These data indicated that an innate immune response is also associated with TBI in Drosophila.

One important cause of secondary injuries in TBI is activation of the innate immune response. The innate immune response is triggered by pathogen-derived molecules and by endogenous molecules generated by stressed and injured cells. A component of this response is the production of proinflammatory cytokines, such as tumor necrosis factor (TNF), by microglial cells and astrocytes. In some studies, elevated levels of TNF in the cerebrospinal fluid of TBI patients are correlated with unfavorable clinical outcomes, providing evidence of the injurious role of cytokines. Likewise, inhibition of TNF shortly after primary injuries in rodents reduces the severity of some deleterious outcomes, such as tissue loss. On the other hand, long-term recovery of neurological damage in TBI is impaired in TNF-deficient mice, providing evidence of a beneficial role of cytokines Therefore, the innate immune response plays a critical but not yet fully understood role in TBI. Flies provide an opportunity to advance our understanding of this role because innate immune response pathways are highly conserved between flies and humans. The Toll pathway in flies is analogous with mammalian Toll-like receptor (TLR) pathways, and the Immune deficiency (Imd) pathway is analogous with the mammalian TNF pathway. Among the key functions of both the Toll and Imd pathways is the transcriptional activation of antimicrobial peptide (AMP) genes. To assess activation of the innate immune response in flies following primary injuries, we used quantitative real-time reverse transcription-PCR (qRT-PCR) to determine AMP gene mRNA levels in heads of w1118 flies subjected to the standard TBI protocol. To control for the usual increase in expression of innate immunity genes that occurs as a function of age, treated flies were normalized to age-matched untreated flies. Flies that survived the standard TBI protocol exhibited an increase in AMP gene expression within 24 h after the primary injuries (FIG. 8). Similar results were observed in 0- to 4-d-old and 20- to 21-d-old flies. Some AMP genes were activated within one hour after the primary injury and all AMP genes were activated within 24 hours.

Activation of innate immunity genes following primary injuries is at least somewhat specific because the expression of other genes such as TAF1 was not similarly increased. Thus, TBI in flies, as in mammals, elicits activation of an innate immune response pathway.

Example 9 Assessing Neuronal Cell Death Following TBI

To determine if TBI can cause Chronic Traumatic Encephalopathy (CTE)-like progressive neurodegeneration in flies, immunocytochemical approaches are used to measure apoptosis in the fly brain. Antibody staining is used to detect activated Caspase 3 (CaspAct), which is produced by Caspase 3 cleavage during apoptosis. TUNEL (Terminal deoxynucleotidyl transferase dUTP nick end labeling) is used to detect DNA fragmentation, which occurs in late stage apoptotic cells. Co-staining of brains with an antibody to Elav is used to identify apoptotic cells that are neurons. The average number of CaspAct-positive and TUNEL-positive neurons per brain is used as a measure of the level of apoptosis. To determine the time course of apoptosis, injured flies are compared to uninjured flies at 5-day intervals after the injury. For each time point tested, at least ten brains are examined, which our experience indicates should be sufficient to uncover significant differences caused by injury.

Longevity is used as another indicator of long-term neurological damage. In humans, TBI significantly reduces longevity relative to the general population. To assay longevity, the number of surviving injured and uninjured flies is determined each day until all of the flies die. In addition to the survival curve, the 50% survival point is used as a measure of longevity. To focus on the long-term effects of injury, flies that die within 5-days of injury are excluded from the analyses.

Climbing is also be used as an indicator of long-term neurological damage. When tapped to the bottom of a vial, flies normally respond by climbing to the top, a behavior called negative geotaxis. It is widely observed that neurodegeneration correlates with reduced climbing ability. To quantitate climbing ability, flies are tapped to the bottom of a vial and allowed to climb for 10 seconds, at which time the number of flies in each quarter of the vial is counted and used for statistical comparison. To determine the time course of effects on climbing, injured and uninjured flies are examined at 5-day intervals after injury. For each longevity and climbing time point tested, at least 200 flies are examined, which our experience indicates should be sufficient to uncover significant differences caused by injury.

In humans, CTE and Alzheimer's Disease (AD) have a similar appearance and are thought to share mechanistic similarities as well. In a *Drosophila* model of AD that is based on expression of human tau protein in all neurons, the Target of rapamycin (TOR) signaling pathway drives cell cycle activation and apoptosis of post-mitotic neurons. In this fly model, as in human AD, tau becomes hyperphosphorylated. To test whether TBI-associated neurodegeneration in flies shares common molecular mechanisms with AD, we will determine if TBI in flies causes neurons to activate the mitotic cell cycle via TOR signaling and/or hyperphosphorylation of tau. Antibody staining of fly brains is used to detect early and late markers of cell cycle activation: PCNA (Proliferating Cell Nuclear Antigen) and PH3 (phosphorylated histone H3 serine 10), respectively. Co-staining with an antibody to Elav will be used to identify neurons. To determine the time course of cell cycle activation, injured and uninjured flies are compared at 5-day intervals after injury. We will also determine whether blocking neuron cell cycle activation by co-expression of Rbf1 (Retinoblastoma factor-1) and Dap (Dacapo) in neurons or inhibiting TOR activity by feeding flies rapamycin block injury-induced neuronal apoptosis, as they do in the fly model of AD. The GAL4/UAS system is used to express Rbf1 and Dap specifically in neurons. To determine whether TBI stimulates hyperphosphorylation of tau, tau phospho-epitope-specific antibodies in ELISAs are used to quantitate the level of phosphorylated tau. Brains of injured and uninjured AD model flies are compared at 5-day intervals after TBI.

Example 10 Assessment of Sleeping Pattern Abnormalities in *Drosophila* Following TBI TBI in humans also causes sleep disorders such as hypersomnia and insomnia. Our preliminary data indicated that TBI in flies affects sleep patterns. We used a well-established assay and instrument (the *Drosophila* Activity Monitoring System from TriKinetics) to monitor sleep and found that injured flies had increased daytime sleep relative to uninjured flies, but nighttime sleep was not affected. We will follow-up on this finding by analyzing other sleep parameters: total sleep over 24 hours, total daytime sleep, average daytime sleep bout length, maximum daytime sleep bout length, and daytime locomotor activity per waking minute. To determine the time course of sleep pattern changes, these sleep parameters are determined over 1-week periods that begin 1, 5, 10 and 20 days after injury.

Example 11 Assessment of Acute Effects of TBI in *Drosophila*

In rodents, and presumably in humans, TBI immediately causes the excessive release of excitatory neurotransmitters such as glutamate. Subsequent activation of glutamate receptors initiates a cascade of events, including cellular influx of $Ca^{2+}$, mitochondrial swelling and impaired ATP synthesis, and oxidative stress. It is possible that these events also occur in response to TBI in flies given that some studies have found that a similar cascade of events is caused by excessive glutamate in the fly brain, and that the glutamate receptor (mGluRA) is expressed in most regions of the neuropil. We will use assays established by Rival et al. (2004), *Curr Biol.*, 14(7):599-605 and others to test the possibility that TBI in flies causes excessive release of glutamate and downstream events observed in rodents. All of the assays compare injured and uninjured fly brains at 1, 2, 8, and 24 hours post-injury. In brief, glutamate release is directly detected in brain sections with an antibody to L-glutamate and indirectly detected by inhibiting glutamate release and determining the effect on downstream events. To selectively inhibit glutamate release from pre-synaptic termini the drug riluzole is fed to flies. The extent of mitochondrial swelling is determined by measuring the diameter of mitochondria visualized by transmission electron microscopy (TEM) of brain sections. ATP levels are measured in brain extracts using a commercially available luciferase-based assay. Lastly, oxidative stress is directly determined by measuring the level of reactive oxygen species (ROS) in brain extracts using a fluorescence-based assay and indirectly determined by measuring the sensitivity of flies to the free radical generator paraquat. The expectation is that if injury generates oxidative stress then injured flies will have increased mortality relative to uninjured flies when fed paraquat.

Example 12 Identifying Genes Associated with TBI Outcomes

A standard approach for identifying genes that underlie developmental and behavioral mechanisms is an unbiased dominant modifier screen. For example, application of this approach has provided substantial insights into human neurodegenerative disorders. A collection of deficiency stocks is screened for suppression or enhancement of TBI-associated lethality at 24 hours after injury. A deficiency stock panel is available from the Bloomington *Drosophila* Stock Center at Indiana University. The collection contains 793 stocks that in total cover 98.4% of the *Drosophila* genome. For each deficiency stock, flies are tested at 7 days and 24 days old. Both ages will be tested because we observe that younger flies have a significantly lower rate of TBI-induced lethality and neurodegeneration than older flies (FIG. 3). Deletions that affect only young or old flies will provide insight into the age-dependent physiological changes that affect TBI outcomes. Deletions whose effect on mortality is more than two standard deviations away from the mean of the collection will be selected for further testing. As proof of principle, we found that 2 of 35 innate immunity gene mutants are two standard deviations away from the mean. The mean lethality rate for 7-day old flies is 64%. In contrast, 7-day old PGRP-LE and TAK1 mutants have lethality rates of 17% and 25%, respectively. Modifying deficiencies will be further characterized if they affect the severity of TBI-induced neurodegeneration, as assayed by the number of vacuoles in the brain. Testing smaller deficiencies and mutant alleles that are contained within modifying deficiencies will be used to identify the relevant modifier gene. Molecular identification of these modifier genes will be confirmed by use of RNA interference and transgenic rescue experiments with the wild type gene.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A method for assaying a test agent in *Drosophila*, the method comprising the steps of:
   (i) delivering to one or more *Drosophila* individuals an impact to induce closed-head traumatic brain injury (TBI) wherein the step of delivering the impact comprises the steps of:
      (a) providing the one or more unrestrained *Drosophila* individuals inside one or more walled containers secured to a spring-loaded acceleration assembly having first and second ends and defining a deflectable long axis therebetween, the assembly fixedly secured at the first end to a base, the one or more containers secured to the assembly at the second end, the assembly configured to accelerate the one or more secured walled containers toward a strike surface upon deflection of the assembly on the long axis followed by release; and
      (b) deflecting the assembly on the long axis and releasing the deflected assembly, thereby accelerating the one or more secured walled containers toward and into contact with the strike surface, whereby the unrestrained *Drosophila* individuals in the one or more walled containers impact the one or more walled containers;
   (ii) dosing the one or more *Drosophila* individuals with a test agent before or after the impact; and
   (iii) after the impact, assessing in the dosed one or more *Drosophila* individuals the severity of a phenotype associated with closed-head TBI selected from the group consisting of lethality, an immune response, neurodegeneration, a sleep abnormality, a circadian abnormality, a learning deficit, a memory deficit, a social behavior deficit, a motor behavior deficit, changes in longevity, changes in intestinal barrier permeability, changes in mitochondrial structure and function, changes in gene expression, changes in enzymatic activity, changes in phosphorylation, changes in post-translational modification, changes in metabolite concentration, changes in cell death, changes in neurotransmitter signaling, and changes in microtubule structure.

2. The method of claim 1, wherein, in step (ii) the dosing is performed before the impact.

3. The method of claim 1, wherein, in step (ii) the dosing is performed after the impact.

4. The method of claim 1, wherein the *Drosophila* individuals are at least 20 days old.

5. The method of claim 1 wherein step (i) comprises delivering the impact to *Drosophila* individuals from at least two different genetic backgrounds.

6. The method of claim 5, wherein step (i) comprises delivering the impact to *Drosophila* individuals from at least ten different genetic backgrounds.

7. The method of claim 1, wherein the one or more walled containers contact the strike surface at a predetermined velocity between about 0.5 m/s and about 20 m/s.

8. The method of claim 1, wherein the acceleration assembly accommodates at least two containers, each container comprising *Drosophila* individuals.

9. The method of claim 1 wherein the test agent is a transgene.

10. The method of claim 9, wherein the transgene comprises an expression cassette for an RNAi.

11. The method of claim 9, wherein the transgene comprises an open reading frame encoding at least one polypeptide.

12. The method of claim 11, wherein the at least one polypeptide is selected from the group consisting of hAPP, hAbeta1-42, a hTau, a hSynuclein, hHuntingtin, a hTDP-43, a hSOD, hLRRK2, a hGSK3β, and a polyQ polypeptide.

13. The method of claim 9, wherein the transgene provides in the one or more individuals a non-coding RNA.

14. A method for assaying a test agent in *Drosophila*, the method comprising the steps of:
   (i) delivering to one or more *Drosophila* individuals an impact to induce closed-head traumatic brain injury (TBI), wherein the step of delivering the impact comprises the steps of:
      (a) providing the one or more unrestrained *Drosophila* individuals inside one or more walled containers secured to a spring-loaded acceleration assembly having first and second ends and defining a deflectable long axis therebetween, the assembly fixedly secured at the first end to a base, the one or more containers secured to the assembly at the second end, the assembly configured to accelerate the one or more secured walled containers toward a strike surface upon deflection of the assembly on the long axis followed by release; and (b) deflecting the assembly on the long axis and releasing the assembly, thereby accelerating the one or more secured walled containers toward and into contact with the strike surface, whereby the unrestrained *Drosophila* individuals in the one or more walled containers impact the one or more walled containers;

(ii) dosing the one or more individuals with a test agent before or after the impact; and (iii) after the impact, assessing closed-head TBI-associated lethality in the dosed one or more *Drosophila*.

15. The method of claim 14, wherein, in step (ii) the dosing is performed before the impact.

16. The method of claim 14, wherein, in step (ii) the dosing is performed after the impact.

17. The method of claim 14, wherein step (i) comprises delivering the impact to *Drosophila* individuals from at least two different genetic backgrounds.

* * * * *